(12) United States Patent
Stewart

(10) Patent No.: US 8,295,919 B2
(45) Date of Patent: Oct. 23, 2012

(54) REDUCED ELECTRODE ELECTROCARDIOGRAPHY SYSTEM

(75) Inventor: Donald-Bane Stewart, Edinburgh (GB)

(73) Assignee: Spacelabs Healthcare, LLC, Issaquah, WA (US)

( * ) Notice: Subject to any disclaimer, the term of this patent is extended or adjusted under 35 U.S.C. 154(b) by 0 days.

(21) Appl. No.: 13/113,184

(22) Filed: May 23, 2011

(65) Prior Publication Data

US 2011/0288425 A1    Nov. 24, 2011

Related U.S. Application Data

(63) Continuation of application No. 10/563,657, filed on May 18, 2006, now Pat. No. 7,974,684.

(30) Foreign Application Priority Data

Jul. 31, 2003  (GB) .................................. 0317947.0

(51) Int. Cl.
*A61B 5/0402* (2006.01)
(52) U.S. Cl. ...................................................... 600/509
(58) Field of Classification Search .......... 600/508–509, 600/512
See application file for complete search history.

(56) References Cited

U.S. PATENT DOCUMENTS

| | | |
|---|---|---|
| 4,106,495 A | 8/1978 | Kennedy |
| 4,121,575 A | 10/1978 | Mills et al. |
| 4,318,412 A | 3/1982 | Stanly et al. |
| 4,569,357 A | 2/1986 | Sanz et al. |
| 4,850,370 A | 7/1989 | Dower |
| 5,058,598 A | 10/1991 | Nicklas et al. |
| 5,490,515 A | 2/1996 | Mortara |
| 5,511,553 A | 4/1996 | Segalowitz |
| 5,678,545 A | 10/1997 | Stratbucker |
| 5,711,304 A | 1/1998 | Dower |
| 5,938,597 A | 8/1999 | Stratbucker |
| 6,052,615 A | 4/2000 | Feild et al. |
| 6,119,035 A | 9/2000 | Wang |
| 6,327,487 B1 | 12/2001 | Stratbucker |
| 6,453,186 B1 | 9/2002 | Lovejoy et al. |
| 6,532,379 B2 | 3/2003 | Stratbucker |

(Continued)

FOREIGN PATENT DOCUMENTS

EP    0845240 A    6/1998

(Continued)

OTHER PUBLICATIONS

"Ventricular Electrocardiography," HURST, J.Willis, M.D. http://www.medscape.com, 1998 260 pages.

(Continued)

*Primary Examiner* — Scott Getzow
*Assistant Examiner* — Amanda Patton
(74) *Attorney, Agent, or Firm* — Novel IP

(57) ABSTRACT

Electrocardiographic (ECG) signals, such as the standard 12-lead, are synthesized from a novel reduced electrode set. Signals are received from a group of electrodes connected to predetermined locations on a human body and deriving at least one further ECG signal using predetermined transformation(s) on a set of ECG signals. This forms a desired set of signals. The group of electrodes may comprise the standard 12 lead electrode sites V2 and V5 plus one electrode positioned substantially level with V5 on the right anterior auxiliary line and a further electrode on each of the right hand side and left hand side of the body. In an alternative arrangement, the electrode position V2 is replaced by an electrode position Vc on the sternum directly between the standard electrode sites V1 and V2. Also disclosed is a method of improving accuracy of synthesized signals by detecting body posture and modifying the transformations.

19 Claims, 13 Drawing Sheets

U.S. PATENT DOCUMENTS

| | | |
|---|---|---|
| 6,690,967 B2 | 2/2004 | Meij et al. |
| 7,277,752 B2 | 10/2007 | Matos |
| 2002/0035334 A1 | 3/2002 | Meij et al. |
| 2002/0045837 A1 | 4/2002 | Kojima et al. |
| 2005/0059896 A1 | 3/2005 | Drakulic |

FOREIGN PATENT DOCUMENTS

| | | |
|---|---|---|
| EP | 1221299 A | 7/2002 |
| WO | WO92/02171 A1 | 2/1992 |
| WO | WO99/55228 A1 | 11/1999 |
| WO | WO01/60250 A1 | 8/2001 |
| WO | WO03/099115 A | 12/2003 |

OTHER PUBLICATIONS

U.K. Search Report Dated Feb. 3, 2004, UK Patent Application No. GB0317947.0, 1 page.

WIPO International Search Report Dated Jan. 20, 2005, International Patent Application No. PCT/GB2004/003324, 6 pages.

ised as U.S. Pat. No. 7,974,684.

REDUCED ELECTRODE ELECTROCARDIOGRAPHY SYSTEM

CROSS-REFERENCE

The present application is a continuation of U.S. patent application Ser. No. 10/563,657 filed May 5, 2006, which has issued as U.S. Pat. No. 7,974,684.

BACKGROUND

The present invention relates to a reduced electrode electrocardiography system. In particular the invention relates to a system for the synthesis of a standard twelve-lead electrocardiograph or similar, from measurements using fewer leads.

The electrocardiograph (or ECG) is one of the most important non-invasive diagnostic tools available to the cardiologist. During the development of electrocardiography, there has evolved a set of standard methods of obtaining an ECG from a subject. These standard methods include the "12 Lead ECG", the "9 lead ECG", the "15 lead ECG" and the "vectorcardiogram".

The 12 lead ECG method is by far the most common of these methods and is thus often referred to as the "standard 12 lead ECG" or even just the "standard ECG". Twelve "leads" (or signals) are obtained from a subject using ten electrodes placed on their skin, placed on standardised locations around the body. Each electrode is connected to a signal processing apparatus via a respective wire (or "lead"). The term "lead" commonly refers to either a physical wire to an electrode or to an ECG signal itself. To avoid confusion here, the use of the word "lead" will always refer to an ECG signal, never to electrode wiring.

The standard 12 lead ECG is divided into two sets: the limb leads I, II, III, aVR, aVL and aVF and the precordial leads V1, V2, V3, V4, V5 and V6.

Unfortunately, the application of the 12 lead ECG is problematic: The use of ten electrodes plus associated wiring often causes discomfort to the subject, even on short timescales. The placement of ten electrodes can take considerable time, particularly if carried out by a non-specialist. Additionally, the amount of electrode wiring can impede the clinician when performing other procedures on the subject, while the cost of the procedure is increased when using a larger number of electrodes.

In the case of "ambulatory" recording, the situation is much worse. During ambulatory recording, measurements are made while the subject is free to move around, for example walking, running etc. The limb electrodes can thus be subject to severe motion and muscular artefacts that corrupt the desired ECG signals. Electrode wiring connected to the arms and legs also restricts the movement of the subject and the clothing that they can wear. The use of a large number of wires increases the opportunity for one or more of these wires to become caught or snagged while the subject is moving, possibly causing electrode detachment or denigration of the electrode/skin contact. In addition, electrode/skin contacts often become irritable if worn for a significant length of time, a problem that is clearly exacerbated by the number of electrodes worn.

Several reduced lead sets methods have been proposed to provide an approximation of a standard ECG using fewer electrodes placed at carefully defined electrode locations. For example U.S. Pat. Nos. 4,106,495, 4,318,412, 4,850,370, 5,058,598, 6,052,615 and 6,119,035 each use methods involving linear transformations between the leads recorded and the desired lead set, typically either the standard 12 lead ECG or the vector cardiogram. All of these systems reduce the difficulty, setup time, discomfort and unit cost of an ECG recording. This is balanced against the inevitable differences between the true standard ECG recording and the synthesised alternative. The use of a reduced set of electrodes is also of significant worth if the ECG must be sent over a communications network, where bandwidth availability may have to be taken into account.

A problem with known reduced electrode sets is that the transformations required to synthesise the desired lead(s) are not constant for different subjects. Known systems have used either fixed transformations (determined over a large population of subjects) to approximate the transformations required, or subject-specific transformations that are calculated per subject, the latter calculation requiring both the desired lead(s) and the reduced lead set to be measured on the subject in question as a preliminary step.

A further problem is that the synthesis transformations are not constant even for the same subject under a variety of body postures. This is because as the subject's body posture changes, so too does their body shape. If the subject maintains the same single posture for which the lead transformations were defined, for example the classic "resting ECG" position where the subject is reclined on their back, then this posture effect will not occur. However an ambulatory subject will exhibit several different body postures and thus posture induced changes in the synthesis transformations become relevant.

Known reduced-set solutions can also be error prone because of lack of familiarity with the non-standard ECG positions they use, and for the same reason, it can be hard to verify accuracy of readings.

SUMMARY

The present invention seeks to provide a system wherein the synthesis of the standard 12 lead ECG is achieved using a reduced number of electrode contacts on the subject. In addition, it is intended that the system will allow for ambulatory movement of the subject. In an alternative, compatible aspect, the system will be less affected by variations in posture.

The system in some embodiments introduces the use of a "temporary lead": a temporary ECG signal generated using at least one additional electrode outside the set of ECG electrode sites that is only measured/recorded/worn for a short period(s) of time.

The system also introduces the use of "unmeasured electrodes" and "unmeasured leads". An "unmeasured electrode site" can be defined as an electrode site on the subject outside the set of electrode sites defined by the electrocardiographic and temporary electrode sites. An "unmeasured lead" can be defined as a lead, that is, a signal that would require the use of at least one unmeasured electrode site to measure or derive directly.

The invention provides methods of the general type comprising synthesizing electrocardiographic (ECG) signals by receiving signals from a first group of electrodes connected to predetermined locations on a human body to acquire a first set of ECG signals and deriving at least one further ECG signal using predetermined transformation(s) on said first set of ECG signals or a subset thereof to form a desired set of signals, wherein the first group of electrodes comprises the standard 12 lead electrode sites V2 and V5 plus at least one electrode positioned substantially level with V5 on the right anterior axillary line, and at least one further electrode positioned on each of the right hand side and left hand side of the body.

The method includes placing said at least one further electrode on each of the right hand side and left hand side of the body substantially level with the upper portion of the limbs.

In a first embodiment of the invention, there is provided a method for obtaining a set of ECG signals of the general type set forth above wherein the electrode sites are located at:

V2: the standard 12 lead electrode site V2;
V5: the standard 12 lead electrode site V5;
V5R: level with V5 on the right anterior axillary line;
RA: the standard 12 lead electrode site RA (arm, shoulder, wrist or hand); and
LA: the standard 12 lead electrode site LA (arm, shoulder, wrist or hand).

In a second embodiment of the invention there is provided a method for obtaining a set of ECG signals of the general type set forth above wherein the electrode sites are located at:

V2: the standard 12 lead electrode site V2;
V5: the standard 12 lead electrode site V5;
V5R: level with V5 on the right anterior axillary line;
RC: on the upper chest of the body, at the same height as the manubrium and on the right mid-clavicle line; and
LC: on the upper chest of the body, at the same height as the manubrium and on the left mid-clavicle line.

In a third embodiment of the invention there is provided a method for obtaining a set of ECG signals of the general type set forth above wherein the electrode sites are located at:

V2: the standard 12 lead electrode site V2;
V5: the standard 12 lead electrode site V5;
V5R: level with V5 on the right anterior axillary line;
R: anywhere in the region of the right hand side of the body, between the front upper chest above the level of the heart and the right arm, shoulder or hand; and
L: anywhere in the region of the left hand side of the body, between the front upper chest above the level of the heart and the left arm, shoulder or hand.

In further embodiments, the invention provides a method for obtaining a set of ECG signals of the general type set forth above wherein the electrode position V2 is replaced by the electrode position Vc which is defined to be on the sternum directly between the standard electrode sites V1 and V2.

In one embodiment the method includes deriving an ECG signal from a temporary electrode that is not connected for the full duration the ECG measurement.

The method may further comprise generating a subject-specific transformation or set of transformations acting on the ECG signals that synthesises a representation of the temporary electrode signal.

A temporary electrode may be reactivated or reapplied at a later time in order to redefine the subject-specific transformations.

The method may further include defining a reference potential for each temporary electrode from one of the following options: the electrical potential of an ECG electrode; the electrical potential of a different temporary electrode or a potential formed by a combination of ECG electrode(s) and/or temporary electrode(s).

A temporary ECG signal may be defined as the potential difference between the potential at the temporary electrode and its reference potential.

The method may further comprise obtaining a set of ECG signals from both the first set of ECG signals and a temporary ECG signal.

The method may further comprise obtaining a second set of ECG signals from the subject using just the first set of ECG signals.

The temporary signal(s) can be synthesised using subject-specific transformations on the second set of ECG signals.

Further ECG signals can be derived using a predetermined transformation or set of transformations on the set comprised from, or a subset selected from, the second set of ECG signals and at least one synthesised temporary electrode signal.

A temporary electrode(s) may be located at any point on the right arm, shoulder or hand.

A temporary electrode(s) may be located at any point on the left arm, shoulder or hand.

The temporary electrode(s) may be connected at a different time from when the first set of ECG signals is acquired, or equivalently, activated temporarily, and the subject-specific transformations retrospectively calculated.

A temporary electrode can, after initial use, be used to perform other functions other than that of supplying electrocardiogram signal data or otherwise cease to operate as electrocardiograph signal electrode, or can be completely removed. For example, it could be used to measure transthoracic impedance.

In a further embodiment, an input connection to the measurement means or device used to obtain a signal from an ECG electrode(s) can have a secondary use to obtain a signal from a temporary electrode.

In a further embodiment, the method can include switching an electrode between separate modes of operation wherein in a first mode, the electrode measures an ECG signal and in a second mode, the electrode forms a reference electrical connection between a subject and an ECG measurement means.

In a further embodiment the method further includes the steps of:

applying a plurality of electrodes on a subject's body to enable the measurement of a set of ECG signals for that subject;
detecting a subject's body posture (for example using a posture sensor on the subject; a posture sensor in the device; a posture selection switch on the device or by any other suitable means); and
applying a set of transformation to the set or a subset of the measured ECG signals in order to form a desired set of ECG signals, wherein said set of transformations are selected or modified according to the measurements of the subjects measured posture.

The body posture sensor may comprise an accelerometer, tilt sensor or manual switch.

In a further embodiment the method further includes the steps of:

calculating a simulation matrix for the at least one temporary signal from the first set of data or a subset thereof;
applying a simulation matrix to the second set of ECG signals to generate a simulated temporary signal; and
applying a fixed derivation matrix to the second data set plus the simulated signal to define an unmeasured ECG lead;
wherein the method can be adapted to compensate for subject specific variations in posture and movement.

The method of deriving unmeasured ECG signals may further comprise forming a matrix R wherein R contains data points from the measured ECG signals. Similarly, a solution matrix A can be calculated from the temporary electrode signals.

The matrix $sX$ can be calculated using $sX(i)=R*A(i)$.

A matrix M can be formed from the first set of ECG signals plus the simulated temporary electrode signals.

The method may further comprise forming the derived matrix $dL(x)=M*B(x)$, where $B(x)$ is a predetermined solution matrix and $dL(x)$ simulates the data that would have been observed at an unmeasured electrode site.

In one embodiment, the method may comprise measuring a first set of ECG signals, processing said signals to derive a standard 12 lead ECG and displaying said standard 12 lead ECG in real time.

In another embodiment, the first set of ECG signals is recorded and stored for later processing to derive a standard 12 lead ECG.

The method may further comprise displaying the derived standard 12 lead ECG signal.

In a further, independent aspect of the invention, there is provided a method for obtaining a set of ECG signals of the general type comprising synthesising electrocardiographic (ECG) signals by receiving signals from a first group of electrodes connected to predetermined locations on a human body to acquire a first set of ECG signals and deriving at least one further ECG signal using predetermined transformation(s) on said first set of ECG signals or a subset thereof to form a desired set of signals, wherein said first group includes at least electrodes located at the following sites:

R and L: placed on or near the right and left upper limbs respectively; and

Vc: placed on the sternum.

Sites R and L may comprise specifically sites RC and LC placed at the same level as the manubrium on the right and left mid-clavicular lines respectively. Signals from these positions can be processed to approximate the standard sites RA and LA, but with less inconvenience in ambulatory mode.

Alternatively, sites R and L may comprise sites RA and LA placed on the right arm and left arm respectively, for example at the wrists.

Site Vc may be located on the sternum directly between the standard electrode sites V1 and V2.

In a further aspect of the invention, there is provided a method for obtaining a set of ECG signals of the general type comprising synthesizing electrocardiographic (ECG) signals by receiving signals from a first group of electrodes connected to predetermined locations on a human body to acquire a first set of ECG signals and deriving at least one further ECG signal using predetermined transformation(s) on said first set of ECG signals or a subset thereof to form a desired set of signals, wherein said first group includes at least electrodes a located at the following sites:

Vm: one of the standard 12 lead electrode sites V4, V5 and V6 (m=4, 5 or 6);

VnR: level with one of the standard electrode sites V4, V5 and V6 (n=4, 5 or 6) on the right midclavicular line, right anterior axillary line or right mid axillary line respectively; and Vc: placed on the sternum.

In a preferred embodiment, m=n, so that VnR is opposite Vm on the right anterior axillary line and is therefore easier to place. In a preferred embodiment, m=n=5, so that the sites Vm and VnR are V5 and V5R respectively.

Vc may be located directly between the standard electrode sites V1 and V2.

In preferred embodiments of the invention, already described above and illustrated further in the specific description and drawings, at least five electrode sites are chosen by combining these two further aspects of the invention, but this is not essential.

In a further embodiment the method includes deriving an ECG signal from a temporary electrode that is not connected for the full duration the ECG measurement.

In a further, independent aspect, the invention provides a method for obtaining a set of electrocardiographic (ECG) signals by:

receiving signals from a first group of electrodes connected to predetermined locations on a human body to acquire a first set of ECG signals;

synthesising at least one further ECG signal using predetermined transformation(s) on said first set of ECG signals or a subset thereof to form a synthesised set of ECG signals, each synthesised signal corresponding to a location on the body (hereinafter referred to as the synthesised location);

detecting the body's posture; and selecting or modifying the transformations used in said synthesising step on the basis of the detected body posture, so as to reduce posture-induced inaccuracies between each synthesised signal and a real signal that would be measured at the synthesised location in a given posture.

This aspect of the invention can be applied to reduced-electrode ECG methods besides the ones specified in the first aspect of the invention and described specifically herein.

The invention further provides an apparatus for synthesising ECG data comprising means arranged to received measured ECG signals and signal processing means arranged to perform the method steps according to any of the aspects of the invention as set forth above.

The invention further provides a system for measuring ECG signals wherein there is provided a subset of the standard 12 lead ECG electrodes and means for storing and processing signals from said subset of electrodes to obtain a standard 12 lead ECG.

The apparatus may comprise an analogue to digital converter for digitising the signals from said subset of electrodes.

The signal processing means may be arranged to implement a linear combination processing array for processing said digitised signals to derive a standard 12 lead ECG. Needless to say, said means can be implemented in dedicated hardware or in software running on a general purpose microprocessor or digital signal processor circuit.

The apparatus may comprise separate units for processing and displaying ECG signals, with means for interfacing the separate units for processing and displaying the ECG signals. The means for processing and displaying the ECG signals can be alternatively integrated together.

The means for storing said signal data may be a portable media format, such as flash card memory.

The invention yet further provides a storage device carrying program instructions for causing a general purpose microprocessor or signal processor circuit to implement a method as set forth above. This may be of use in implementing the invention using existing ECG and/or computer hardware.

BRIEF DESCRIPTION OF THE DRAWINGS

Embodiments of the invention will now be described, by way of example only, by reference to the accompanying drawings, in which.

DETAILED DESCRIPTION OF THE EMBODIMENTS

Figure 1:
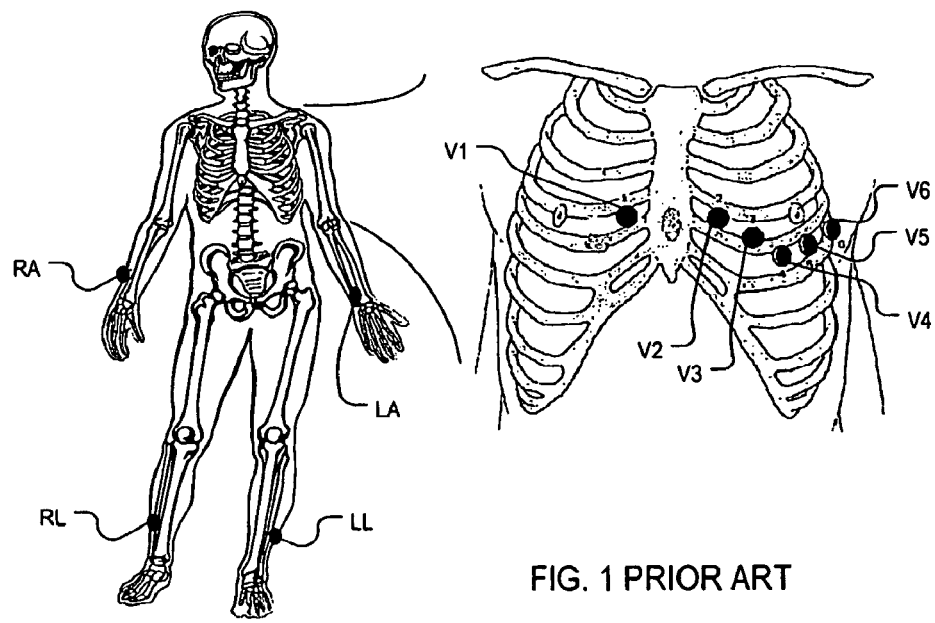
FIG. 1 illustrates electrode positions in a standard 12 lead electrocardiograph system.

FIG. 1 illustrates a standard 12 lead electrocardiograph (ECG) system well known in the art where twelve "leads" (or signals) are obtained from a subject using ten electrodes placed on their skin. These electrodes are placed in standardized locations as follows: Electrode RA on the right wrist; electrode LA on the left wrist; electrode LL (or F) on the left ankle; electrode RL (or reference) on the right ankle; electrode V1 on the fourth intercostal space to the right of the sternum; electrode V2 on the fourth intercostal space to the left of the sternum; electrode V4 in the fifth intercostal space at the left mid-clavicular line; electrode V3 between V2 and V4; electrode V5 level with V4 at left anterior axillary line and electrode V6 level with V5 at left mid-axillary line. Note that often the limb electrodes are placed on the upper arms or upper legs of subjects: this shift causes only very minor changes to the standard 12 lead ECG. However, when ambulatory movement of the subject is required, for example during a "stress-test" wherein the subject is required to physically exercise during the ECG recording, the limb electrodes are moved to the torso to avoid motion and muscle artifacts, in the ECG signals. This severe shift in electrode positions can cause notable changes in the observed ECG.

The standard 12 lead ECG is divided into two sets: the limb leads and the precordial leads. Combinations of the limb electrodes form the limb leads: these leads are named I, II, III, aVR, aVL and aVF. Each precordial lead is formed between one of the six "V" electrodes and the average of RA, LA and LL (also known as the Wilson Terminal). The precordial leads are named V1, V2, V3, V4, V5 and V6.

Figure 2:
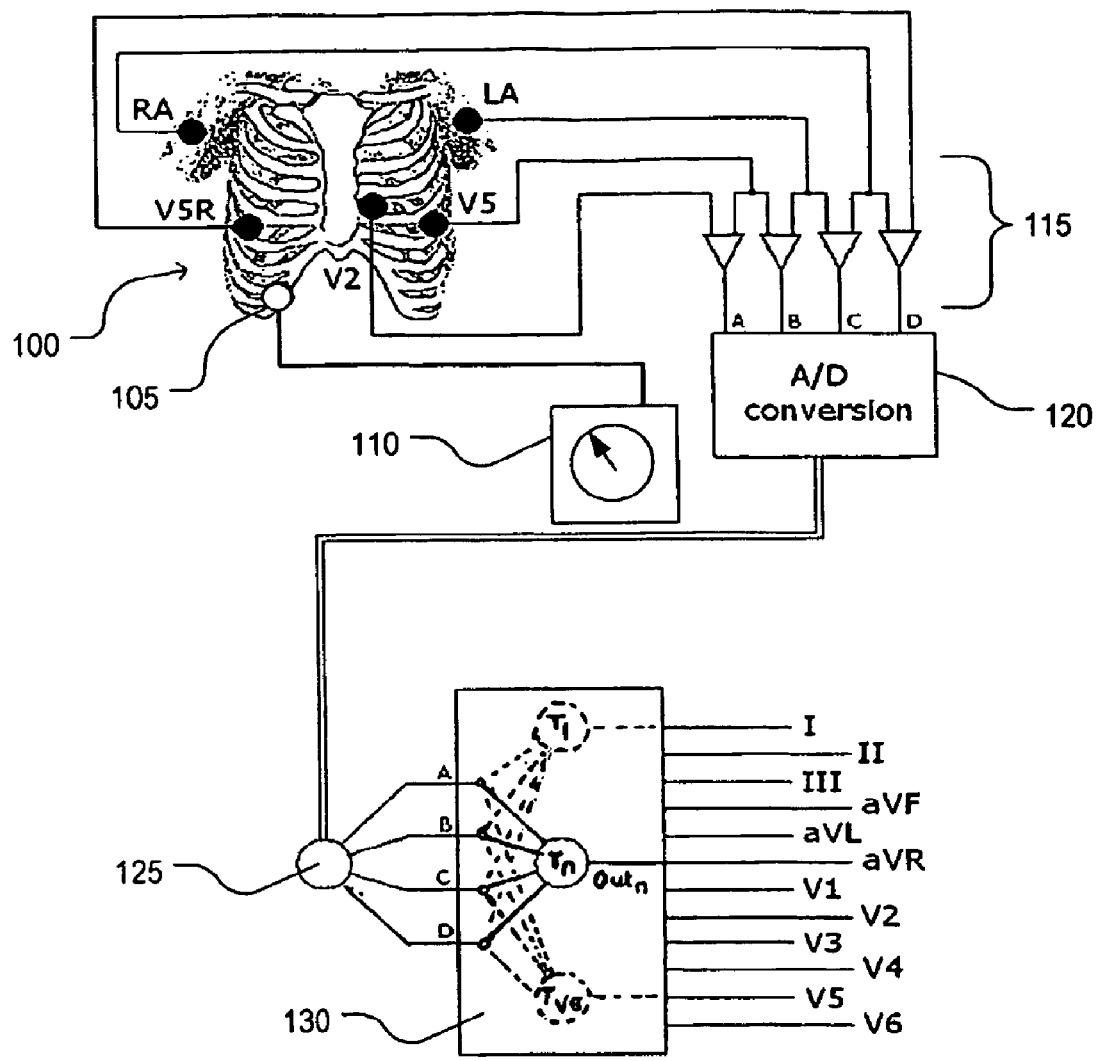
FIG. 2 illustrates a system for obtaining a set of electrocardiographic leads using a reduced electrode set.

FIG. 2 shows a novel system suitable for synthesising a set of ECG leads, in this case the standard 12 lead ECG leads described above, using a reduced electrode set.

Shown here are a number of electrodes V2, V5, V5R, RA and LA attached to a subject's body 100.

The electrode sites are located at:

V2: the standard 12 lead electrode site V2

V5: the standard 12 lead electrode site V5

V5R: level with V5 on the right anterior axillary line

RA: the standard 12 lead electrode site RA (arm, shoulder, wrist or hand)

LA: the standard 12 lead electrode site LA (arm, shoulder, wrist or hand).

There is also shown an optional reference lead 105 that may be connected to an instrument reference potential 110 generated by the instrument. Signals from the electrodes are fed into differential amplifiers 115, producing signals A, B, C and D which are input into analogue to digital signal converter 120. The converted signals are input to a demultiplexer 125 and into a linear combination processing array 130. Only three elements $T_1$, $T_{v5}$, $T_n$ of the array are shown here for clarity and illustration but in practice any number suitable for the task may be used. The outputs of the array are the synthesised leads as shown.

The output of each array element is:

$$out_n = T_n(A, B, C, D)$$
$$= (A * k_a) + (B * k_b) + (C * k_c) + (D * k_d)$$

Each $T_n$ therefore is a linear combination of $\{A, B, C, D\}$ where $T_n$ has a defined set of weights $\{k_a, k_b, k_c, k_d\}$.

This system can be used as the basis of a method to synthesise an ECG lead using a predetermined transformation or transformations on the set comprised of, or a subset selected from, the set of gathered ECG data gathered from the five electrodes.

The description of the system will refer to "unmeasured leads" and "temporary leads". An "unmeasured lead" is defined as a lead of the standard 12 lead set (or other desired set) that would require the use of at least one "unmeasured electrode site" to measure or derive directly. An "unmeasured electrode site" is defined an as an electrode site of the standard set on the subject outside the set of electrode sites defined by the ECG and temporary electrode sites. Thus one can derive an unmeasured lead using ECG data gathered from a reduced electrode set. For a temporary lead, a temporary ECG signal generated using at least one additional electrode outside the ECG electrode sites that is only connected or measured for a short period of time.

Figure 3:
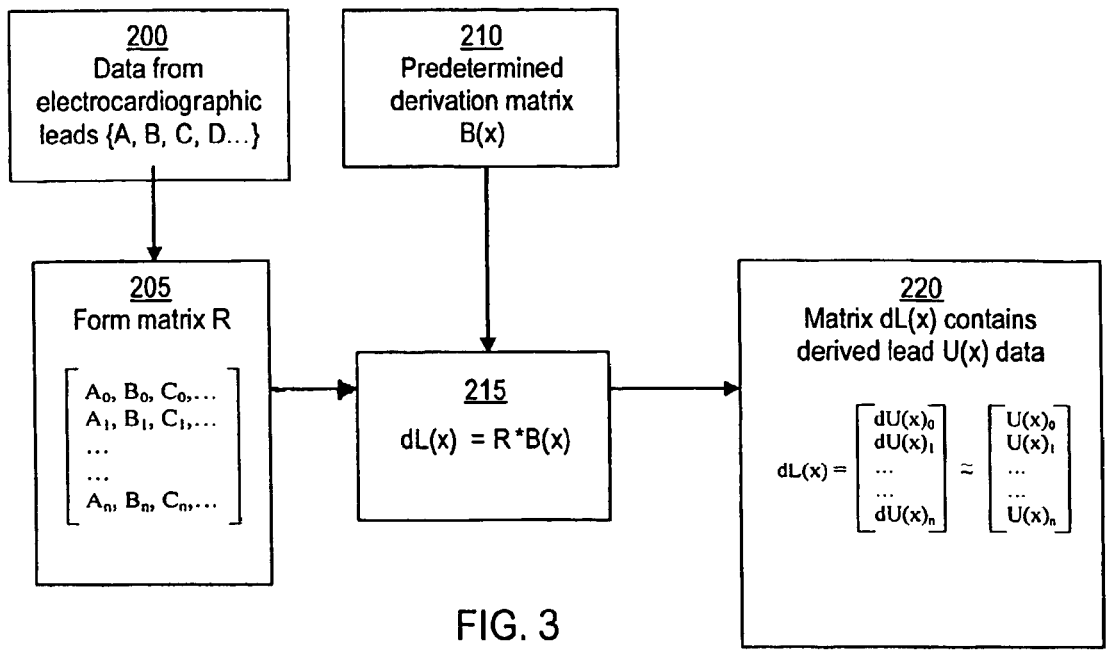
FIG. 3 illustrates steps in the derivation of an unmeasured lead using a fixed predetermined matrix.

FIG. 3 illustrates the derivation of an unmeasured lead using a fixed predetermined matrix.

In this example, data 200 from a set of ECG leads is used to form a matrix R 205. R contains data points from the set of measured leads used. Matrix R is multiplied 210 by a predetermined derivation matrix B(x) 215 to produce a derived lead matrix dL(x) 215 which contains an approximation to the data U(x) for the unmeasured leads data.

Figure 9:
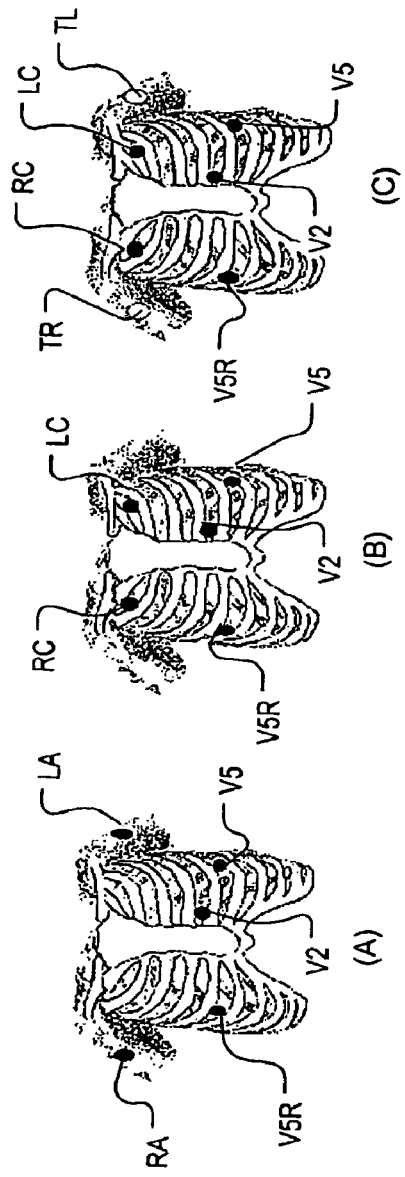
FIG. 9 shows electrode site locations for different modes of operation of an electrocardiograph system.
Figure 10:
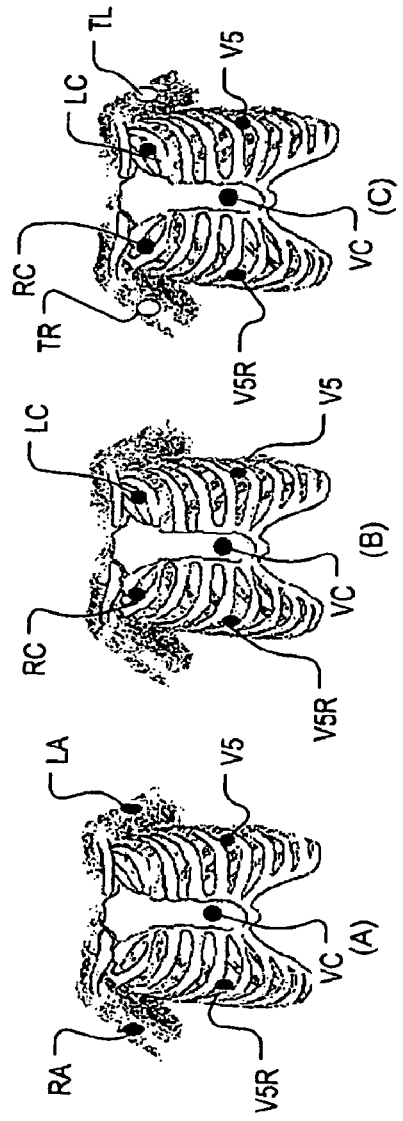
FIG. 10 shows alternative electrode site locations for different modes of operation of an electrocardiograph system.

The measured lead set is not limited to the one illustrated in FIG. 2 and described above. Several variations and enhancements will now be described. These find applications in different operational modes, to be described later and illustrated with reference to FIGS. 9 and 10 in particular.

It is possible to replace electrodes of the above set with others, and synthesise leads. For example, it is possible to replace the RA and LA electrodes with the following alternative arrangement:

RC: on the upper chest of the body, at the same height as the manubrium and on the right mid-clavicle line.

LC: on the upper chest of the body, at the same height as the manubrium and on the left mid-clavicle line.

One can gather a set of ECG data from these electrodes and derive new ECG lead data for RA and LA electrodes using a predetermined transformation or set of transformations as described above.

The electrode position V2 can also be replaced by the electrode position Vc that is defined to be on the sternum directly between the standard electrode sites V1 and V2.

Vc is placed directly above bone: although this is considered to be slightly worse for a resting ECG (static patient) it produces better results for an ambulatory ECG (moving patient). Other factors may influence the choice of Vc over V2, such as the physiology of a patient or presence of injuries which might impede electrode placement.

It is also possible to define a "temporary lead" using a similar technique. One first applies at least one "temporary electrode" to the subject, where a temporary electrode is defined as an electrode that is not used to obtain ECG data continuously for the full duration of the ECG measurement. When not in use as an electrocardiograph signal electrode, which may occur either once or a number of times before, during or after the ECG measurement, the temporary electrode can be removed, disconnected, disabled, ignored, and/or used to perform a function other than that of supplying electrocardiogram signal data, or otherwise cease to operate as electrocardiograph signal electrode.

Figure 4:
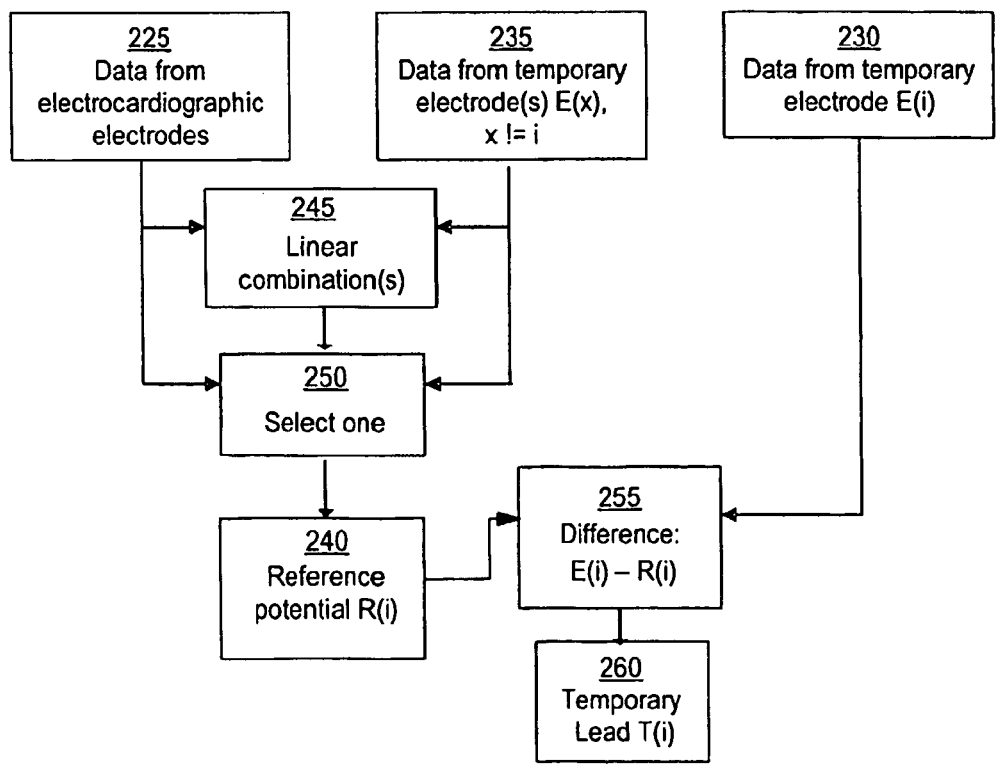
FIG. 4 illustrates steps in the definition of a temporary lead.

FIG. 4 shows the definition of a temporary lead.

A set of data 225 is gathered from the ECG electrodes. Data 230 is also gathered from a temporary electrode E(i) and optionally, additional data 235 gathered from other temporary electrodes E(x, x≠i).

For each temporary electrode, a reference potential 240 is defined, either from the electrical potential of an ECG lead electrodes 225, or the electrical potential of a different temporary electrode 235, or from the potential formed by a combination 245 of ECG lead electrode(s) 225 and/or temporary electrode(s) 235.

Data is selected 250 from the three possible choices and a reference potential R(i) 240 calculated. A difference 255 is calculated from the data from the temporary electrode E(i) 235 and reference potential R(i) 240 to synthesise each temporary electrode, where a temporary lead, T(i) 260 is defined as the potential difference between the potential at the temporary electrode and its reference potential.

One can generate a subject-specific transformation or set of transformations acting on the ECG leads that synthesises a representation of the temporary lead. This same transformation or set of transformations remains applicable for the given subject using the given ECG lead set. Thus on the collection of a second set of ECG data, the temporary lead can be synthesised using the subject-specific transformation or set of transformations on the second set of ECG data at any given time.

Using the methodology for temporary leads described above, the ECG leads can be synthesized from data taken from the following electrode sites:

V2: the standard 12 lead electrode site V2
V5: the standard 12 lead electrode site V5
V5R: level with V5 on the right anterior axillary line
R: Anywhere in the region of the right hand side of the body, between the front upper chest (above the level of the heart) and the right arm, shoulder or hand
L: Anywhere in the region of the left hand side of the body, between the front upper chest (above the level of the heart) and the left arm, shoulder or hand.

Further, the electrode position V2 can be replaced by the electrode position Vc, defined to be on the sternum directly between the standard electrode sites V1 and V2.

The electrode sites 'R' and have an added advantage in that they are easy to locate. No specific knowledge of human anatomy is required.

The temporary electrode(s) can be located at any point on the right or left arms, shoulders or hands. The temporary electrode(s) can be applied at a later time, or equivalently, activated temporarily, and the subject-specific transformations retrospectively calculated. The temporary electrode(s) can be re-activated or re-applied at a later time in order to redefine the subject-specific transformations.

It is also possible to configure an input connection to the measurement means used to obtain data from an ECG lead (or leads) to have a secondary temporary use as the means to obtain data from a temporary electrode.

It is possible to modify the electrode apparatus described above to switch between different modes of operation. In a first mode of operation, the electrode attachment is connected to a signal electrode on the subject and used in the measurement of an ECG signal from said subject. In a second mode of operation, the electrode attachment is connected to a reference electrode on the subject (which may or may not be the same electrode as in the first mode of operation) to form a reference electrical connection between the subject and the ECG measurement means.

Although the standard 12 lead ECG has been used as an example in the above descriptions, it should be clear that this method could be applied to any ECG lead set. Note that according to the specific technology of the measurement/recording apparatus, a reference electrode may be attached to the subject. Generally, additional input circuitry can be included in the recording or measurement device to enable data to be gathered from the temporary electrodes.

Operational Modes

The system and methodology described above can be used in a number of modes. The three main modes of operation will now be described: non-ambulatory, generic ambulatory and subject specific. In non-ambulatory mode, the subject is considered to be static (not moving) while in both generic ambulatory and subject-specific modes, the subject is considered to have some degree of freedom of movement.

In the non-ambulatory mode of use, two arm electrodes are included in the electrode placement system. In ambulatory modes such limb electrodes are unsuitable due to motion and muscle artefacts. Hence the arm electrodes are moved to fixed locations on the upper chest and the transformations used to synthesise the standard leads are modified.

Figure 5:
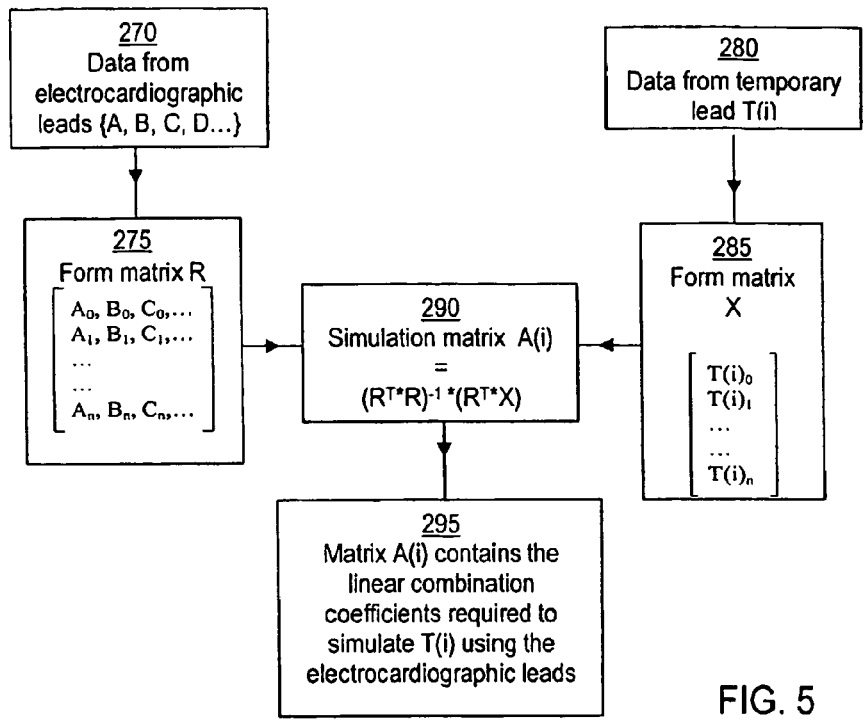
FIG. 5 illustrates the calculation of an adaptive simulation matrix for a temporary lead.

FIG. 5 illustrates the calculation of an adaptive simulation matrix for a temporary lead.

Data 270 is recorded from a set of ECG leads and used to form matrix R 275. Temporary lead T(i) data 280 is gathered and used to form matrix X 285. A simulation matrix A(i) 290 is calculated using matrices R and X. The matrix A(i) contains the linear coefficients required to simulate 295 T(i) using only the ECG leads to gather the data 270.

Figure 6:
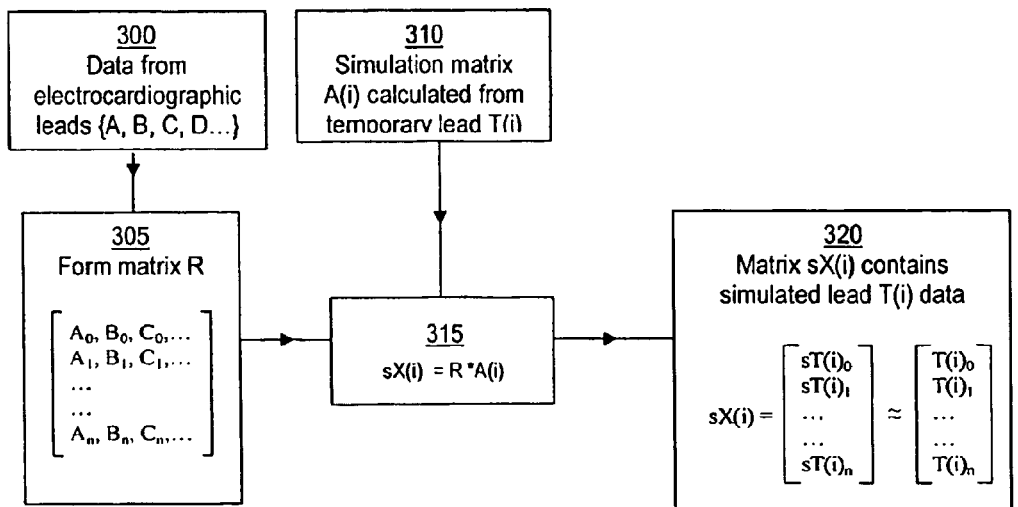
FIG. 6 illustrates the simulation of a temporary lead using a previously determined adaptive matrix.

FIG. 6 illustrates the simulation of a temporary lead using a previously determined adaptive matrix. Data 300 from a set of ECG leads is to form matrix R 305. A simulation matrix A(i) 310 is calculated from the temporary lead in the manner illustrated in FIG. 5. A new matrix sX(i) 315 is calculated from matrices R and A(i). The new matrix Sx(i) contains all the simulated lead data 320.

Figure 7:
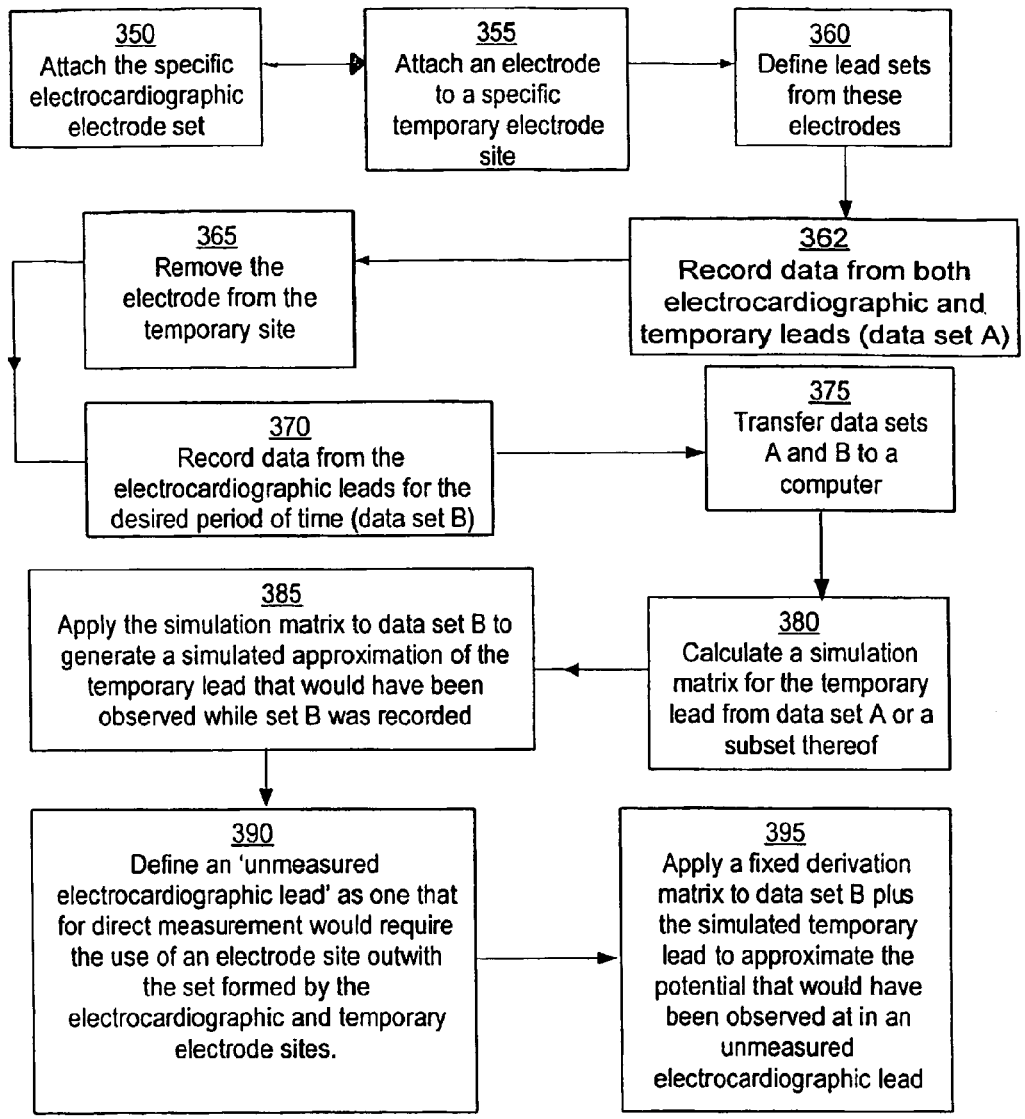
FIG. 7 illustrates a hybrid method of unmeasured lead derivation.

FIG. 7 illustrates a hybrid method of unmeasured lead derivation.

This illustrates how one can use both fixed predetermined and adaptive temporary lead matrices to derive an unmeasured lead using a specific ECG electrode set 350 and a temporary electrode 355. A lead set 360 is defined and a first data set "A" collected 362 from these electrodes. Next, the temporary electrode is removed 365.

A second data set "B" 370 is now recorded for the desired amount of time. A minimum of one full heart beat is required in the simulation data, that is, approximately two seconds of recorded data. However, it is desirable to measure over multiple heart beats in order to minimise noise effects and improve confidence in the transform stability. This is balanced against the cost of greater inconvenience to the subject. In practice, eight to ten seconds is enough to gather sufficient data without causing the procedure to become overly long.

Both data sets A and B are transferred, for example to a computer, for processing 375. A simulation matrix 380 is calculated for the temporary lead from the data set A or a subset thereof. The simulation matrix is then applied to data set B to generate a simulated approximation 385 of the temporary lead that would have been observed while data set B was recorded. An unmeasured ECG lead 390 is defined, that is, a lead that for direct measurement would require the use of an electrode site outside the sets 362, 370 formed by the ECG and temporary electrode sites 350, 360.

Finally, a potential value 395 is calculated by applying a fixed derivation to the data set B plus the simulated temporary lead to approximate the potential that would have been observed at an unmeasured ECG lead.

Figure 8:
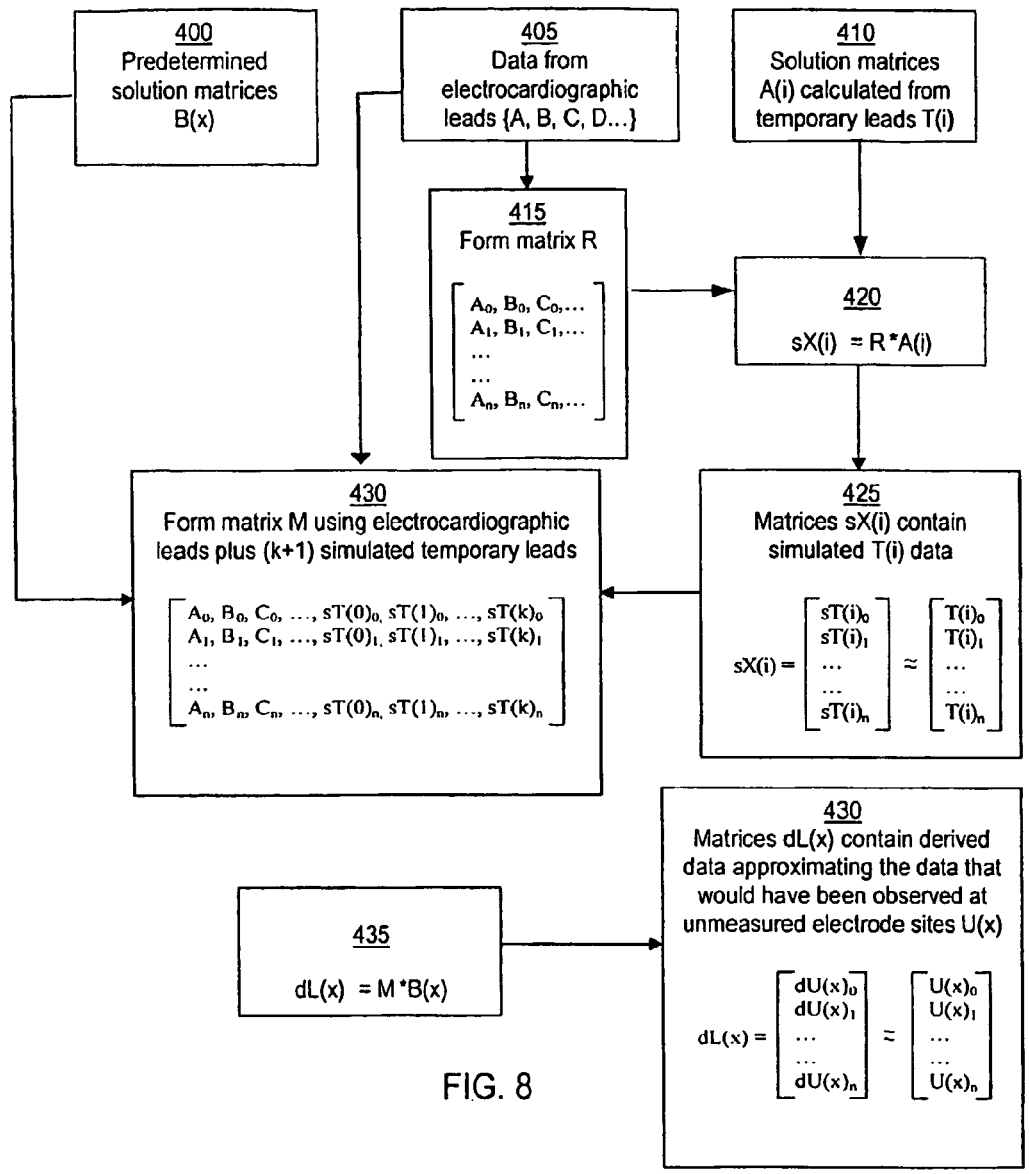
FIG. 8 illustrates the signal processing of the hybrid method of FIG. 7 in greater detail.

FIG. 8 illustrates the signal processing of the hybrid method of FIG. 7 in greater detail.

There is a predetermined solution matrix B(x) and data 405 collected from ECG leads. Solution matrices A(i) 410 are calculated from temporary leads T(i). A first matrix R 415 is formed from the data 405. A matrix sX(i) 420 is calculated from R and A(i). The matrix sX(i) contains the simulated T(i) data 425. A second matrix M 430 is formed using ECG leads plus (k+1) simulated leads.

The matrices B(x) 400 and M 430 are used to form matrices dL(x) 435. The matrices dL(x) contain the derived data approximating the data that would have been observed at unmeasured electrode sites U(x).

In both the generic ambulatory mode and the non-ambulatory mode of operation, fixed transformations act on a defined set of leads to generate the required standard ECG leads. Using the above methodology, it is also possible to achieve a subject-specific ambulatory mode.

The subject-specific ambulatory mode is a significant improvement over the generic ambulatory mode of operation, as it counteracts much of the variability in lead synthesis caused by variations in the body shapes of different subjects. It also allows for greater tolerance regarding the misplacement of electrodes on the subject.

Non-Ambulatory Mode

In the non-ambulatory mode of use the subject under consideration is static, typically either seated or lying prone. In the non-ambulatory mode of use, two arm electrodes are included in the electrode placement system.

FIG. 9A shows electrode site locations for the non-ambulatory mode of operation of an electrocardiograph system. Five electrodes are placed on the subject as shown in FIG. 9A. These positions are comprised of the standard 12 lead electrode sites RA; LA; V2; V5 plus the site "V5R" (level with V5 on the right anterior axillary line).

The standard 12 lead ECG is derived as defined below:
Modelled Left Leg Electrode:

$$mLL=1.083*(V5R-V2)-0.309*(RA-V5)$$

Wilson Central Terminal:

$$W=(RA+LA+mLL)/3$$

Limb Leads:

$$I=LA-RA$$

$$II=mLL-RA$$

$$III=mLL-LA$$

$$aVR=RA-(LA+mLL)/2$$

$$aVL=LA-(RA+mLL)/2$$

$$aVF=mLL-(LA+RA)/2$$

Precordial Leads:

$$V1=0.495*(V2-W)-0.279*(V5-W)$$

$$V2=V2-W$$

$$V3=0.780*(V2-W)+0.512*(V5-W)$$

$$V4=0.324*(V2-W)+0.922*(V5-W)$$

$$V5=V5-W$$

$$V6=-0.126*(V2-W)+0.737*(V5-W)$$

Generic Ambulatory Mode

The generic ambulatory mode takes into consideration movement by the subject, but is non-subject specific.

FIG. 9B shows electrode site locations for the generic ambulatory mode modes of operation of a electrocardiograph system. The two arm electrodes are moved to fixed locations on the front of the upper chest as shown in FIG. 3B. The electrodes RC and LC are placed at the same level as the manubrium on the right and left mid-clavicular lines respectively. Due to the shift in position of these electrodes, the RA and LA electrodes are modelled using fixed transformations:
Modelled RA Electrode:

$$mRA=RC+0.012*(RC-V5)-0.428*(RC-V5R)$$

Modelled LA Electrode:

$$mLA=LC-0.274*(LC-V5)-0.222*(LC-V5R)$$

The standard 12 lead ECG is then derived as described above for the non-ambulatory mode, using the modelled electrodes mRA and mLA as direct replacements for the true electrodes RA and LA.

Subject-Specific Mode

The subject-specific ambulatory mode uses the same electrode setup as for the generic ambulatory mode, but in addition, arm electrodes are temporarily applied (or if applied long-term, are only temporarily used to measure electrocardiogram data). The temporary electrodes supply data that are used to define subject-specific transformations between the electrocardiographic leads and the temporary electrode potentials. These subject-specific transforms allow the potentials at the temporary electrode sites to be synthesised at any time using only the data gathered from the ECG leads.

The set including both the ECG leads and the synthesised electrode potentials is used to generate a model of the left leg electrode using a fixed set of predetermined transformations.

The initial ECG leads plus additional signals generated from the synthesised electrodes and the modelled left leg electrode are used to synthesise the standard ECG leads using a fixed set of predetermined transformations.

The subject-specific mode forms a hybrid methodology between fixed transformation systems and fully subject-adaptive transformation systems. With respect to the former, the hybrid method advantageously generates a better representation of the true standard ECG lead(s). With respect to the latter, the hybrid method advantageously does not require the true standard ECG lead(s) for the given subject to be measured at any point of the process.

For example, a simulated model of the left leg electrode is used in preference to a true electrode connection. This significantly simplifies the subject hook-up procedure, as clothing and subject modesty often hinder access to the left leg.

In order to counteract body posture causing changes to the required transformations, a posture sensor is placed on the subject. The posture measurement is then used to select the appropriate transformation from a set of predetermined or subject-specific options. In the subject specific mode of operation, the set of posture-specific transformations may require to be determined using a plurality of postures of that subject (standing, lying on back, lying on right hand side etc.).

FIG. 9C shows electrode site locations for the subject-specific mode of operation of an electrocardiograph system. The electrodes are placed as for the generic ambulatory mode. After placing the fixed electrodes on the subject, temporary connections TR and TL are made to the subject's left and right arms (or wrists or hands ideally) as shown. This need not be done simultaneously or in the given order. It is envisaged that the temporary connections will be simple metallic contacts that can be held in the subject's hand, thus causing little or no inconvenience to the subject. Conventional electrodes or limb clamps can also be used.

The accuracy required when placing electrodes RC and LC is less critical in the subject-specific mode of operation in comparison to the generic mode, as much of the misplacement error is counteracted by the use of the subject-specific transformations. This is an intended benefit of the hybrid system, designed to ease the process of electrode application.

A subset of the measured leads is used to synthesise the temporary electrodes. The selected subset frees one of the input wires to the ECG measurement means. This "free input" is then used as the means to make the temporary electrode connection(s). This method is highly advantageous as it avoids the need for additional input(s) to the ECG measurement means.

In an alternative embodiment, a reference electrode is incorporated that, during the electrocardiogram measurement, is used to establish a reference electrical connection between the subject and the measurement means. However, before (or after) the electrocardiogram measurement the function of the reference electrode connection is changed to that of a "temporary electrode" connection as described above to enable the collection of data for the subject-specific mode of operation. Again, this advantageously avoids the need for an additional input to the ECG measurement means. However, the data measured for the subject-specific transformations is gathered without the noise suppression benefits of a reference electrode.

In a further enhancement of the method, two electrodes are temporally switched in function: the first from a reference connection to a signal connection and the second from a signal connection to a reference connection. If the original reference electrode is placed at the desired temporary electrode site, this switch allows a "free input" method of synthesising the temporary electrode potential without requiring the user to change electrode connections. Thus the process outlined above can be automated. After the required signal data is read from the temporary electrode site, the electrode functions are returned to their original states. In practice, this switching need be performed once, from "temporary" to "reference".

The subject-specific transformation needed to generate the synthesised equivalent of electrode RA is determined by solving the following matrix equation:

Define Matrix R as:

column 0=$RC-V5$, column 1=$RC-V5R$

Define Matrix X as:

column 0=$RA-RC$

And so Calculate Solution Matrix:

$$A=(R^T*R)^{-1}*(R^T*X)$$

Giving Synthesised RA Electrode:

$$sRA=RC+A_0*(RC-V5)+A_1*(RC-V5R)$$

Similarly, the synthesised equivalent of electrode LA is determined by solving the matrix equation:

Define Matrix L as:

column 0=$LC-V5$, column 1=$LC-V5R$

Define Matrix Y as:

column 0=$LA-LC$

And so Calculate Solution Matrix $$B=(L^T*L)^{-1}*(L^T*Y)$$

Giving Synthesised LA Electrode:

$$sLA=LC+B_0*(LC-V5)+B_1*(LC-V5R)$$

These subject-specific synthesised electrodes are then used as replacements for the true RA and LA electrodes in the transformations defined for the non-ambulatory system defined above.

Posture Sensitivity

The quality of derived ECG data can be improved by incorporation data regarding the subject's body posture. Data relating to a subject's body posture can be measured using a posture sensor on the subject. Alternatively, a posture sensor in the electrocardiograph lead device can be used and the device can be switched between operational modes.

A set of transformations can be selected or modified on the basis of the subject's body posture and an ECG lead derived using the selected set of transformations on the ECG lead data and/or data derived from these ECG leads.

Subject posture measurement means are used in addition to the ECG measurement in order to counteract changes in posture causing changes in the set of transformations required. The subject's posture measured at any given time, for example, standing, lying on right-hand side etc., is used to select an appropriate set of transformations for that given posture.

For the non-ambulatory and generic ambulatory modes of operation, each resolvable subject posture is allocated its own fixed set of transformations.

In a subject-specific mode of operation, each resolvable subject posture requires a subject-specific set of transformations to be generated while the subject adopts the posture in question. The time needed to enact this process may be inconvenient in practice. It is possible to predefine subsets of subject postures, for example, all lying postures, and allocate a single set of subject-specific transformations. Thus only a limited number of all the resolvable postures need be adopted by the subject when gathering the data required for generating the subject-specific transformations. From a limited subset of posture transform coefficients, interpolation between the measured limited subset could be used to form a larger set for additional accuracy.

In one possible mode of operation, the subject posture measurement resolves only two postures: torso horizontal (reclined) and torso vertical (upright). The posture measurement device can be a 1-D accelerometer aligned to the vertical axis of the subject's torso when said subject is in an upright posture. When the acceleration due to gravity measured by this device is less than 0.5 g, then the subject is considered to be in a reclined posture. Otherwise the subject is considered to be upright.

The transformation sets required for these two posture states (upright and reclining) are defined as follows.

Posture-Sensitive Non-Ambulatory Mode

When the subject is upright the transformations are as detailed above for the standard non-ambulatory mode.

When the subject is reclining the transformations are as above for the standard non-ambulatory mode except for the following:

$$mLL=1.065*(V5R-V2)-0.281*(RA-V5)$$

$$V1=0.445*(V2-W)-0.215*(V5-W)$$

$$V3=0.713*(V2-W)+0.622*(V5-W)$$

$$V4=0.252*(V2-W)+1.031*(V5-W)$$

$$V6=-0.093*(V2-W)+0.713*(V5-W)$$

Posture-Sensitive Generic Mode

When the subject is upright the transformations are as described above for the standard non-ambulatory mode.

When the subject is reclining the transformations are:

$$mRA=RC+0.019*(RC-V5)-0.398*(RC-V5R)$$

$$mLA=LC-0.194*(LC-V5)-0.274*(LC-V5R)$$

mRA and mLA are substituted for RA and LA in the reclining non-ambulatory mode process above.

Posture-Sensitive Subject-Specific Mode

In this mode, two sets of subject-specific transformations for synthesising the temporary RA and LA electrodes are calculated. The first is calculated when the subject lying on their back and second when the subject sitting or standing upright. The standard 12 lead ECG is the derived as follows.

When the subject is upright, the subject-specific transformations are used for synthesising electrodes sRA and sLA. Leads sRA and sLA are substituted for RA and LA in the upright non-ambulatory mode process above.

When the subject is reclining the subject-specific transformations are used for synthesising electrodes sRA and sLA. Leads sRA and sLA are substituted for RA and LA in the reclining non-ambulatory mode process above.

Alternative Electrode Sites

FIGS. 10A to C show alternative electrode site locations for different modes of operation of an electrocardiograph system. When the site V2 is difficult to use due to ambulatory restrictions, it is replaced with the electrode site Vc, defined to be on the sternum directly between the standard electrode sites V1 and V2 as shown.

mRA, mLA, sRA and sLA are all independent of the V2 or Vc choice; no V2 term is used. As the subject specific mode just uses the generic case precordial equations with a slightly different W (due to the use of sRA, sLA rather than mRA and mLA), then the descriptions for the generic case are sufficient.

This change in electrode site position enforces the following changes to the above-described transformations.

FIG. 10A shows the case for the non-ambulatory mode.

When the subject is upright the transformations for this case are as above except for the following:

$$mLL=1.096*(V5R-Vc)-0.288*(RA-V5)$$

$$V1=0.607*(Vc-W)-0.116*(V5-W)$$

$$V2=1.269*(Vc-W)+0.291*(V5-W)$$

$$V3=0.997*(Vc-W)+0.723*(V5-W)$$

$$V4=0.420*(Vc-W)+1.015*(V5-W)$$

$$V6=-0.155*(Vc-W)+0.704*(V5-W)$$

When the subject is reclining the transformations for this case are as above except for the following:

$$mLL=1.089*(V5R-Vc)-0.271*(RA-V5)$$

$$V1=0.619*(Vc-W)-0.096*(V5-W)$$

$$V2=1.440*(Vc-W)+0.246*(V5-W)$$

$$V3=1.009*(Vc-W)+0.786*(V5-W)$$

$$V4=0.359*(Vc-W)+1.095*(V5-W)$$

$$V6=-0.126*(Vc-W)+0.693*(V5-W)$$

FIGS. 10B and 10C show the cases for the generic or subject specific modes respectively. The changes here are as described above for the alternative sites for the non-ambulatory mode, but with reference to the Vc modified non-ambulatory mode process.

Dual Purpose Mode

Figure 11:
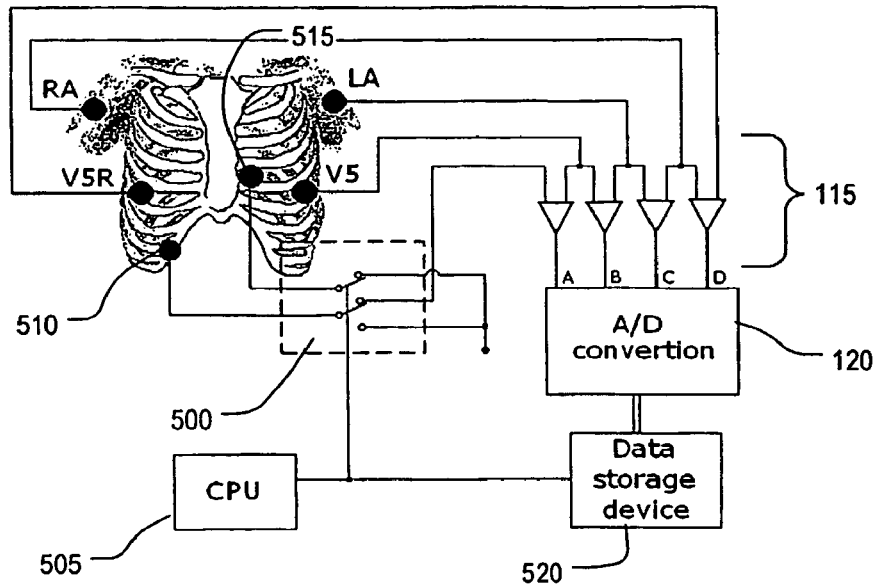
FIG. 11 shows a dual purpose electrode connection.

FIG. 11 shows a dual purpose electrode connection. This arrangement is similar to that shown in FIG. 2, with the addition of a switching matrix 500 controlled by CPU 505. This controls the input of combined reference and temporary electrode 510 and combined V2 and reference electrode 515. A storage device 520 is also shown, and which can record ECG data.

This use of a twin set of dual purpose electrodes 510, 515 has the advantage that there is always a reference electrode connection made at any time and the same numbers of input channels are read at any given time.

This arrangement allows for the measuring an electrocardiogram of a subject incorporating an electrode attachment that can be switched between separate modes of operation. In a first mode of operation, the electrode attachment is connected to a signal electrode on the subject and used in the measurement of an ECG signal from the subject. In a second mode of operation, the electrode attachment is connected to a reference electrode on the subject to form a reference electrical connection between the subject and the ECG measurement means. In the second mode, the electrode may or may not be the same electrode as in the first mode of operation.

Figure 12:
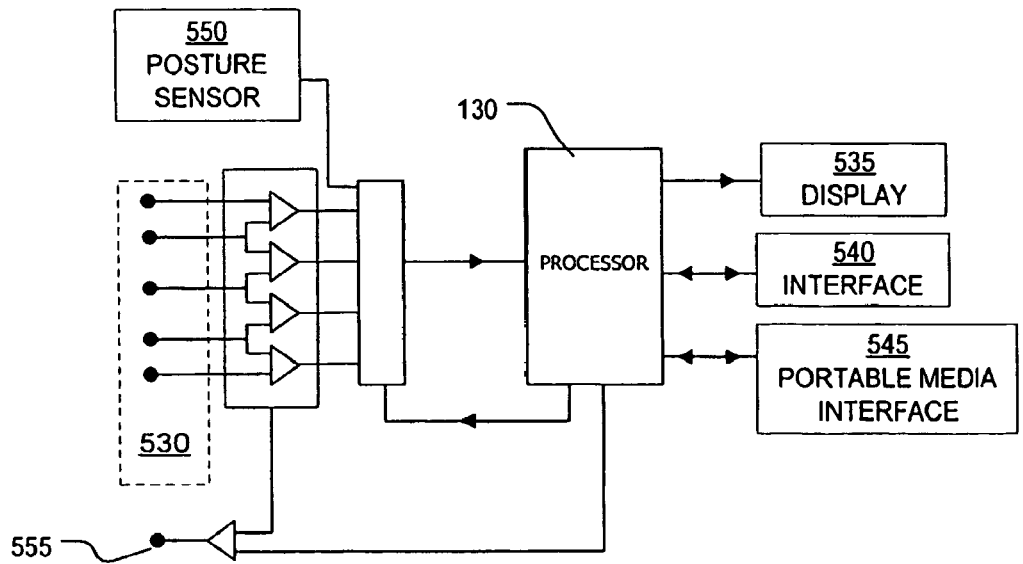
FIG. 12 is a block diagram of an apparatus suitable for recording a posture sensitive electrocardiograph.

FIG. 12 is a block diagram of an apparatus suitable for recording an ECG, showing in more detail the basic apparatus shown in FIG. 2, and possible variations to the basic setup to allow measurements to be made as set out above. Like numerals show like elements.

In addition to the basic apparatus consisting of electrode connections 530, ECG amplifiers 15, processor 130, there is provided display 535, an external computer interface and portable storage media interface 545. The external computer may be any suitable computer, for example a laptop or personal computer. The portable storage media similarly could be any suitable for storing the amount of data generated, for example a flash memory card.

The apparatus can also have components to perform additional functions to enable an ECG to be measured according to the methods set out above. For example, a posture sensor 550 can be connected to the multiplexor and 120. An industry standard "driven" reference electrode 555 can also be provided.

One can expand the apparatus to include a switching matrix 500 shown in FIG. 11 and discussed above to allow electrodes to be used in different modes.

Figure 13:
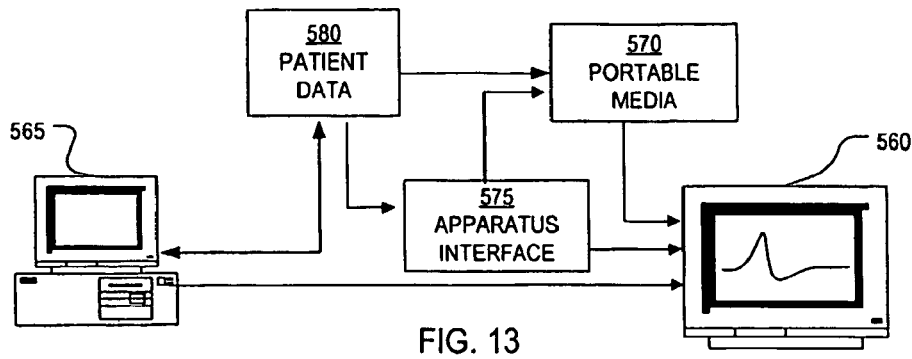
FIG. 13 is a block diagram showing the flow of information between elements of an apparatus for measuring electrocardiograph.

FIG. 13 is a block diagram showing the flow of information between elements of a system for measuring ECG.

There is provided an ECG recorder/monitor 560 for recording and displaying ECG data. There can be further provided a computer 565, portable media 570, an interface 575 for the ECG recorder/monitor 560, and a database 580 of the relevant data required for the creation of an ECG trace.

The information needed to produce the ECG can be held in any suitable format and can include patient identification information, non-ambulatory, generic or patient specific transform coefficients and the recorded ECG data.

The non-ambulatory and generic coefficients, being fixed and known, do not strictly need to be stored externally. However, doing so permits the same procedure to be applied for all three cases of derived 12 lead calculations.

The recorder/monitor 560 can derive data for displaying an ECG trace from a variety of different sources and via a number of different pathways, depending on the setup used.

For example, both patient identification info and transform coefficients can be placed onto the portable storage media 565, for example on a compact flash card, while external to the apparatus, such that when inserted into the apparatus and verified by the user, will be accepted by the apparatus as valid data.

Alternatively, the patient data can be retrieved by the computer 560 and input to the ECG recorder/monitor 560 directly by means of an appropriate interface, for example, IEEE 1394 (Firewire), USB, or wireless protocols. The patient data can also be input directly using the ECG recorder/monitor 560 using interface 575.

In the preferred embodiment, the ECG data is kept in its original form as long as possible. The transformation from a reduced set of leads to a larger set of leads just adds to the memory storage or output signal bandwidth required.

Lead transformation occurs within the apparatus for the following cases: calculating patient specific coefficients within the apparatus, viewing current/previous transformed lead data on a display on the apparatus itself, outputting current/previous transformed lead data to a generic device, for example, a 12 lead ECG display screen designed for a standard input of 12 leads of ECG data.

Lead transformation occurs on a separate computer when calculating patient specific coefficients offline from data provided by the apparatus. As the 'separate' computer must contain software that is compatible with the apparatus transformation scheme, it effectively acts as an extension of the apparatus in this instance.

When data is directly downloaded from a computer, one can perform the required matrix transformations within the computer and output the derived 12 lead ECG data directly to the ECG recorder/monitor 560.

Similarly, data from the ECG recorder/monitor 560 can be downloaded onto portable storage media and the data uploaded into a computer. The computer can perform the required calculations to produce the derived 12 lead ECG data, which can then be input to the recorder/monitor.

Figure 14:
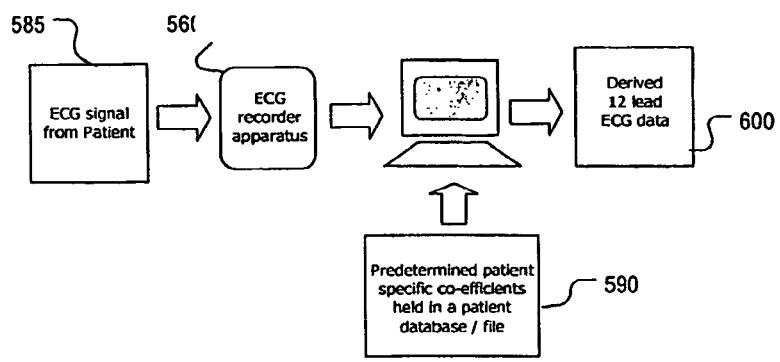
FIG. 14 is a block diagram showing the relationship between calculations in an apparatus for measuring electrocardiograph.

FIG. 14 is a block diagram illustrating calculation pathways in an apparatus for measuring ECG. This shows a computer 565 which processes ECG signal data 585 from ECG recorder/monitor 560 using predetermined patient specific coefficients 590 held in a patient database or file to calculate the derived 12 ECG data 600.

While it is advantageous to have access to the specific transformation coefficients for a given patient before/during setup of the monitoring/recording process, it is not necessary. Patient specific coefficients can be determined at a later time and applied retrospectively to the recorded data so long as the same (or very nearly the same) electrode positions are used.

As the predetermination of patient specific coefficients requires additional setup time, it may be advantageous for some patient screening processes not to spend time determining these coefficients unless the patient reports relevant symptoms after the recording has been made. If a patient reports relevant symptoms, the specific coefficients may be determined after the recording is complete. Generic coefficients are used until such time as patient specific coefficients are calculated.

For example, an ECG signal form a patient can be amplified and digitised for storage directly onto portable storage media such as compact flash. In this case the recording is made without patient specific transforms being performed. Untransformed ECG data is stored on the compact flash card along with generic transform coefficients.

For repeated screening, the patient may already have a set of patient specific transform coefficients. There is a time saving if this set of coefficients is used rather than calculating new coefficients per recording. The predefined coefficients can be uploaded into the apparatus prior to recording, as discussed above, or can be accessed and applied to the ECG data in an external computer containing software that is compatible with the apparatus transformation scheme.

Figure 15:
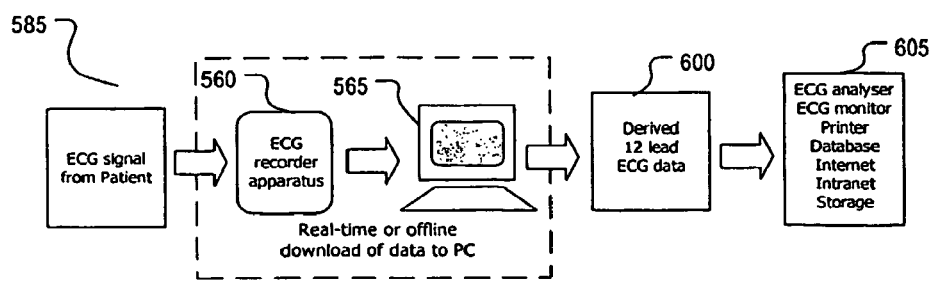
FIG. 15 is a block diagram of a derived 12 lead recorder implementation.

FIG. 15 is a block diagram of an alternative derived 12 lead ECG recorder. This is similar to the implementation shown in FIG. 14 except that here the computer component 600 is explicitly incorporated within the monitor apparatus and the derived 12 lead data calculated in real time and displayed on the monitor display. The derived 12 lead output can be similarly output to the appropriate means 605 to be analysed, recorded and/or output to printers, databases, transmitted across an intranet or the Internet, or stored.

Operation of the Apparatus

Figure 16:
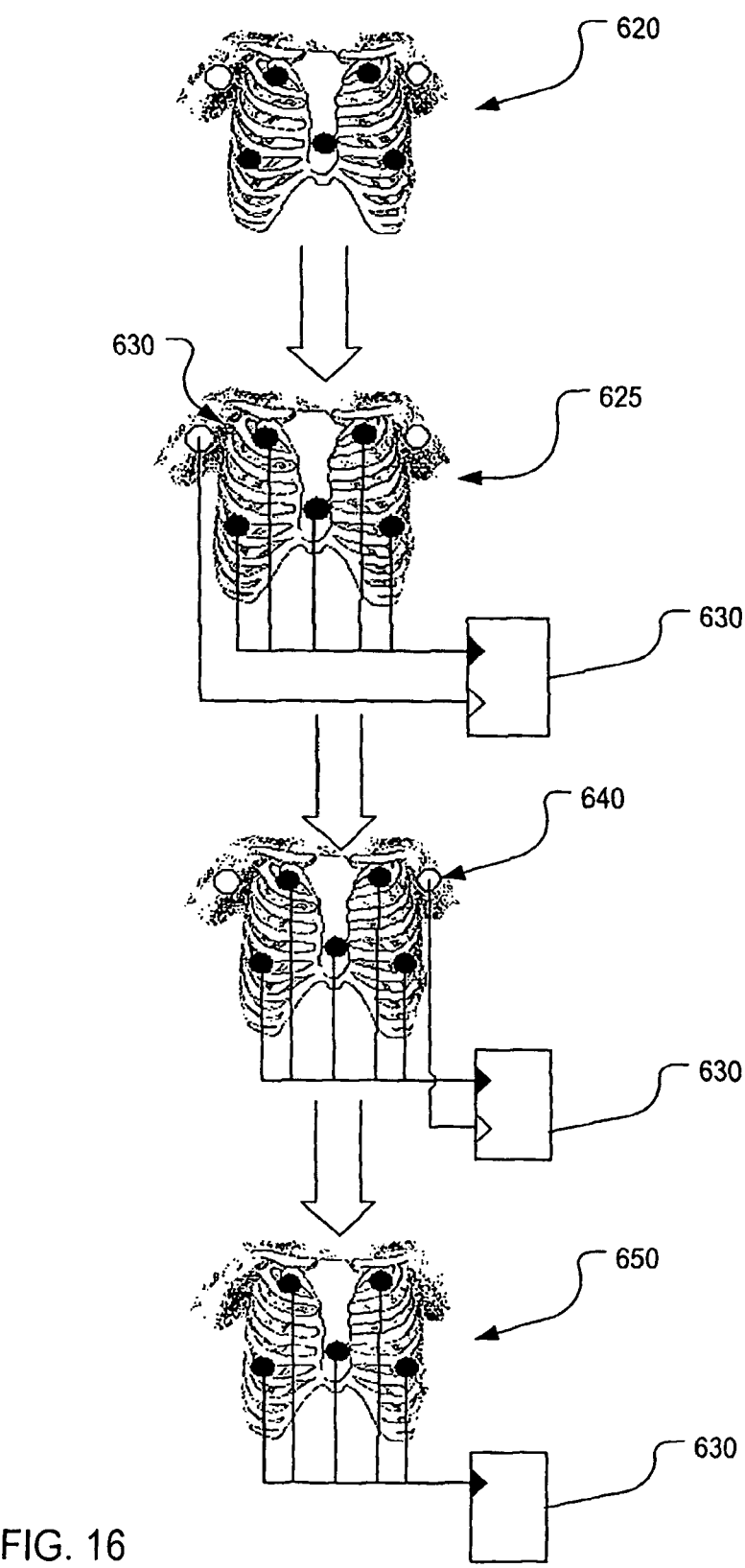
FIG. 16 is a flow diagram of patient specific use of an apparatus for measuring an electrocardiograph using temporary electrodes.

FIG. 16 is a flow diagram of patient specific use of an apparatus for measuring ECG using temporary electrodes.

This shows the steps used in the apparatus using an additional input for temporary electrode and offline patient specific co-efficient calculation.

In a first step, the electrodes are first placed on the locations illustrated. Black filled dots represent "permanent" electrodes while the white dots indicate temporary electrodes. The temporary electrodes can be placed anywhere on the arm/hand in question.

In a second step 625 the ECG recorder/monitor apparatus cable is then connected to the fixed electrodes and the right arm temporary electrode. The recorder/monitor 630 is used to "learn" the right-arm electrode site, that is, the apparatus records all ECG signals for later analysis and co-efficient determination. An alternative implementation would be to derive the coefficients in real time within the apparatus.

In a third step 640 the cable is then disconnected from the right arm electrode and reconnected to the left arm electrode. The recorder/monitor 630 is used to "learn" the left-arm electrode site", that is, the apparatus records all ECG signals for later analysis.

In a fourth step 650 the temporary lead cable is then disconnected and the temporary electrodes removed from the patient.

In one embodiment, reusable "cuff" electrodes are used. It is also possible to use metallic contact that is held in the hand. The temporary cable is connected to this electrode and the entire electrode and cable assembly is moved between the temporary electrode site locations.

Figure 17:
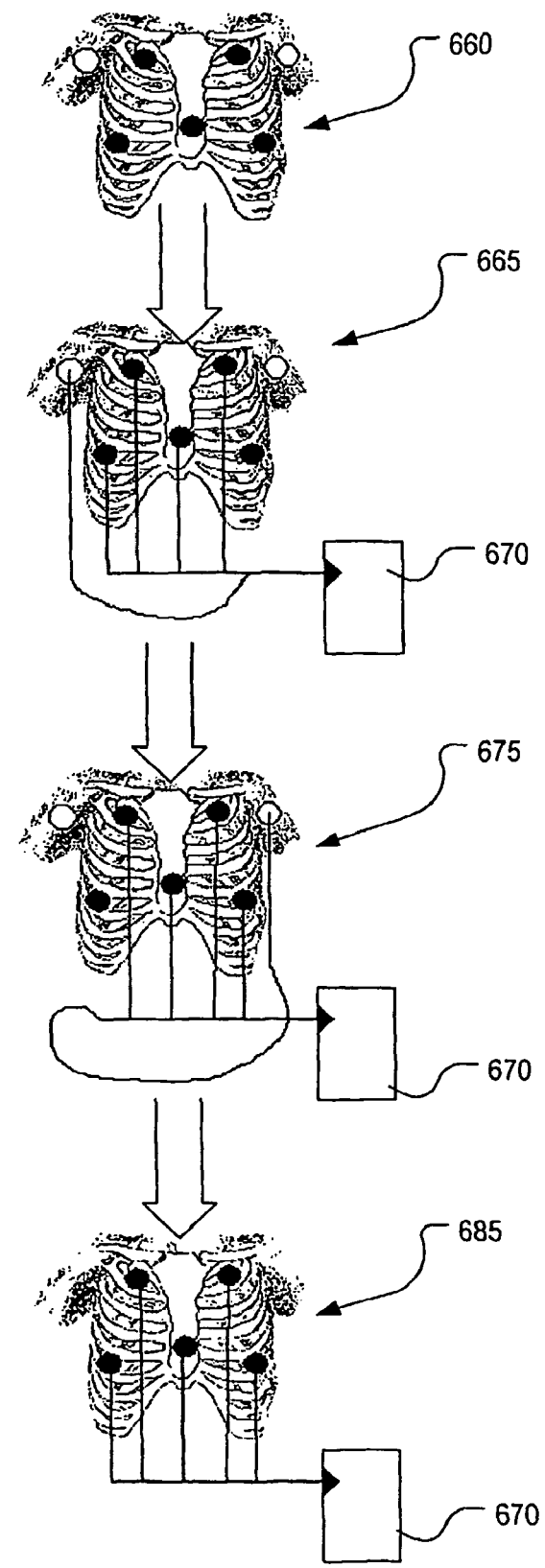
FIG. 17 is a flow diagram of patient specific use of an apparatus for measuring an electrocardiograph using a subset of permanent electrodes to model temporary electrodes.

FIG. 17 is a flow diagram of patient specific use of an apparatus for measuring ECG using a subset of permanent electrodes to model temporary electrodes.

In this case, a subset of the "permanent" electrodes is used to model the temporary electrode site potential plus the offline patient specific co-efficient calculation. This has the advantage that no additional cable connection to the apparatus is required.

In a first step 660, the electrodes are placed at the locations illustrated. Again, black filled dots represent "permanent" electrodes while white dots indicate temporary electrodes. The temporary electrodes may be placed anywhere on the arm/hand in question.

In a second step, the recorder/monitor cables are connected to the subset of fixed electrodes and the right arm temporary electrode as shown. The recorder/monitor 670 will then "learn" right-arm electrode site, that is, the apparatus records all ECG signals for later analysis and co-efficient determination. An alternative implementation would derive the coefficients in real time within the apparatus.

In a third step 675, the cable from the right arm electrode is disconnected and reconnected to the V5 electrode. The V5R electrode cable is disconnected and attached to the left arm electrode. The recorder/monitor 670 then "learns" the left-arm electrode.

In a fourth step 685, the cable to the V5R electrode is re-connected from the right arm electrode and the temporary electrodes removed from the patient.

Figure 18:
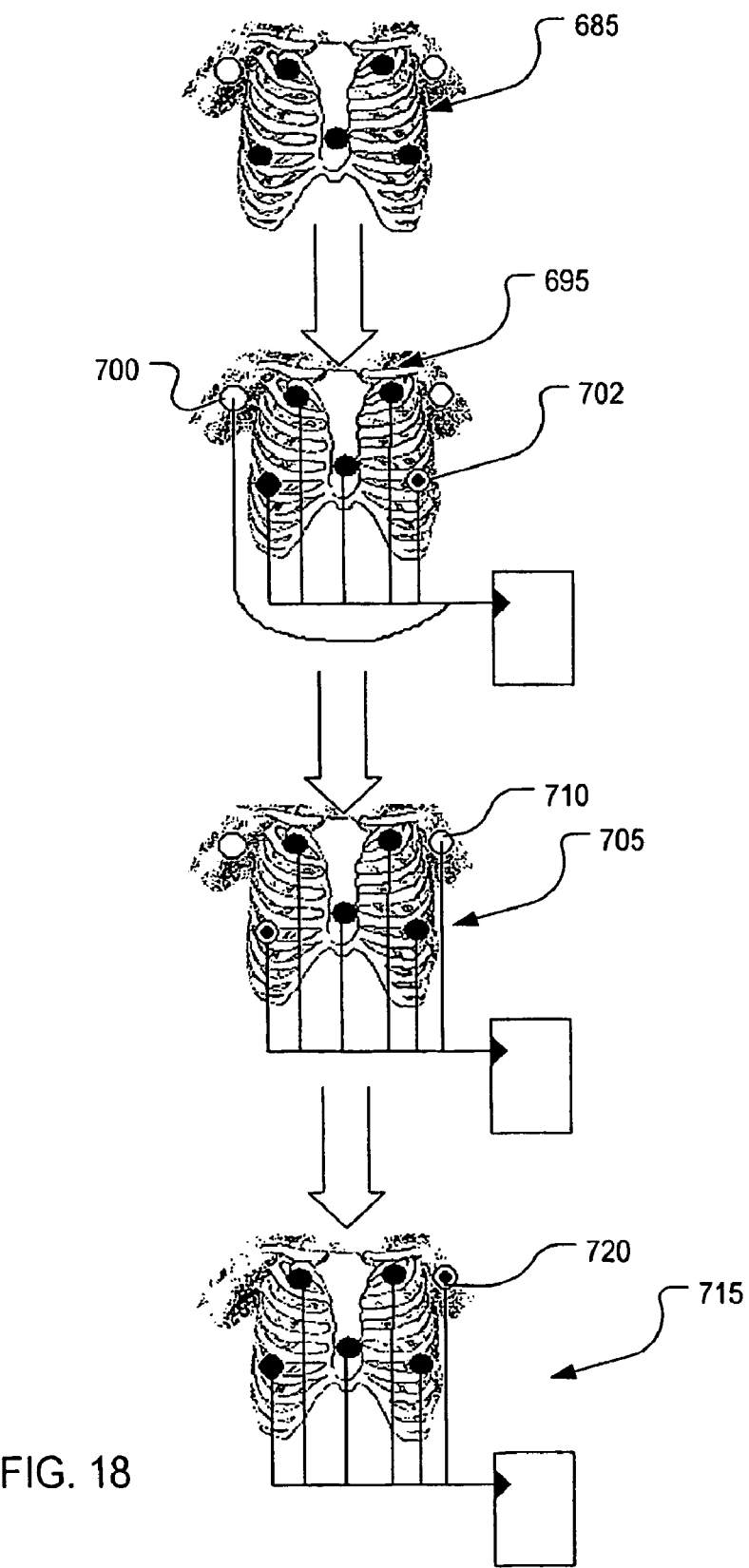
FIG. 18 is a flow diagram of patient specific use of an apparatus for measuring an electrocardiograph using switchable reference electrodes.

FIG. 18 is a flow diagram of patient specific use of an apparatus for measuring ECG using switchable reference electrodes.

This shows the case where the apparatus uses "switchable" reference electrodes and uses a subset of the "permanent" electrodes to model the temporary electrode site potential (and offline patient specific co-efficient calculation). This has the advantage that no additional cable connection to the apparatus is required, plus the normal noise-suppression advantages of a reference lead.

In a first step 685 the electrodes are placed at the locations illustrated. The arm electrodes may be placed anywhere on the arm/hand in question. In this instance, only the right arm electrode is temporary: the left arm electrode is used both as a temporary signal electrode and as the recording reference electrode.

In a second step 695 the apparatus cable is connected to the subset of electrodes shown, including the right arm temporary electrode 700. The right-arm electrode site is "learned". The apparatus sets the reference lead to V5R and records ECG signals for later analysis and co-efficient determination. The reference lead is indicated here by a "target" symbol 702.

In a third step 705 the cable is disconnected from the right arm electrode and connected to the left arm electrode. The apparatus "learns" the left-arm electrode site: the apparatus sets the reference lead to −V5R and records ECG for later analysis.

In a fourth step 715 the temporary right arm electrode is removed and the ECG recorded. The apparatus sets the reference lead to the left arm 720 and records the ECG. If desired, the reference (left arm) electrode could be moved to any location on the body once its function as a temporary signal lead has been completed.

Figure 19:
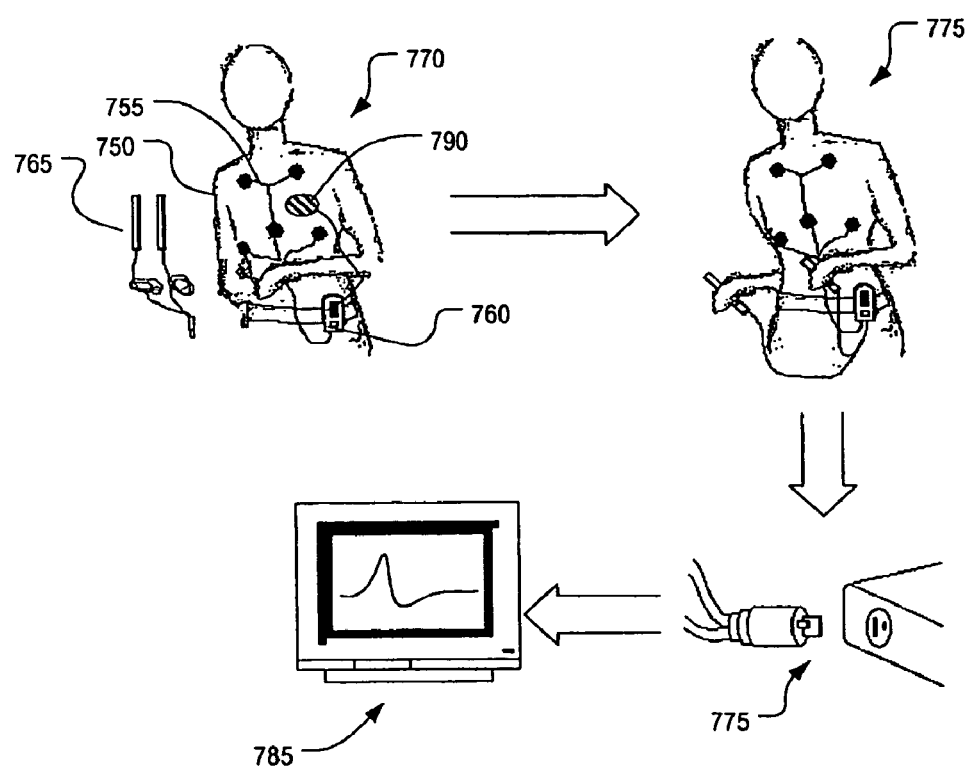
FIG. 19 illustrates a system for measurement of electrocardiograph using temporary electrodes.

FIG. 19 illustrates a system for measurement of ECG using temporary electrodes. This utilises the methods described above.

This shows a patient 750, a set of attached electrodes 755 connected to a recording apparatus 760 for recording ECG signals, and a set of temporary electrodes 765.

In a first step 770, the fixed electrodes 755 are attached to the patient 750 and connected to the recording apparatus 760. The two temporary electrodes 765 are shown including their wiring to an input jack. When connected to the apparatus 760, the apparatus automatically detects the connection and enters a patient specific co-efficient learning mode. The temporary electrodes can be in the form of metallic "handles".

In a second step 775, two temporary signals are input to the apparatus simultaneously: the patient holds a metallic contact in each hand to form the temporary electrode contacts. This enables both right and left arm temporary electrode connections to be established. This makes for a very fast, simple and inexpensive method as the temporary electrodes are reused and connection to the patient is very quick and easy.

The recording apparatus 760 automatically detects when the handles are held by the patient using a standard lead-resistance circuit, and automatically starts obtaining and recording the required signals for calculating specific coefficients to reproduce the two temporary "arm" contacts. Alternatively, it is also possible to determine the transform coefficients from the data as it is input to the apparatus.

The metallic contacts are then unplugged 780. This triggers the apparatus to exit learning mode. The recording 785 may then be manually started, or starts automatically.

Clearly the temporary "electrodes" in this implementation can be replaced with many other simple alternatives, for example, arm or wrist band electrodes or finger clip electrodes.

The recording apparatus 760 shown can also be provided with a position sensor 790 attached. The position sensor can be realised as an accelerometer attached the patient 750 which detects movement and transmits changes in posture to the apparatus 760. The output of the linear processing array 130 is now $out_n = T_n(A, B, C, D, P)$ such that each $T_n$ has a set of weights $\{k_a(P), k_b(P), k_c(P), k_d(P)\}$ that is a function of the posture value P.

The complete system for recording the ECG data can conveniently packaged into a small portable device which can be carried by a patient during recording, attached to a belt, harness, etc. The device can include suitable interfaces for transferring the recorded data, for example by transfer onto a flash memory card or by a wireless connection.

The invention claimed is:

1. A method of synthesizing electrocardiographic (ECG) signals comprising receiving signals from a first group of electrodes concurrently connected to predetermined locations on a human body to acquire a first set of ECG signals and deriving at least one further ECG signal by applying transformation(s) on said first set of ECG signals, or a subset thereof, to form a desired set of signals, wherein the first group of electrodes comprises a V5 12 lead electrode site, a V2 12 lead electrode site, at least one electrode positioned substantially level with V5 on the right anterior axillary line, at least one electrode positioned on a right hand side of the body and at least one electrode positioned on a left hand side of the body, wherein said ECG signals are synthesized from data obtained from less than ten electrode sites.

2. The method of claim 1, wherein said electrodes on the right hand side and left hand side of the body are placed on the torso substantially level with the upper portion of the limbs.

3. The method of claim 1 wherein the electrode sites are located at:
V2: the standard 12 lead electrode site V2;
V5: the standard 12 lead electrode site V5;
V5R: level with V5 on the right anterior axillary line;
R: anywhere in the region of the right hand side of the body, between the front upper chest above the level of the heart and the right arm, shoulder or hand; and
L: anywhere in the region of the left hand side of the body, between the front upper chest above the level of the heart and the left arm, shoulder or hand.

4. The method of claim 1 wherein the electrode sites are located at:
V2: the standard 12 lead electrode site V2;
V5: the standard 12 lead electrode site V5;
V5R: level with V5 on the right anterior axillary line;
RC: on the upper chest of the body, at the same height as the manubrium and on the right mid-clavicle line; and
LC: on the upper chest of the body, at the same height as the manubrium and on the left mid-clavicle line.

5. The method of claim 1 further comprising the step of deriving an ECG signal from a temporary electrode that is not connected for the full duration the ECG measurement.

6. The method of claim 5 further comprising the step of defining a reference potential for the temporary electrode from one of the following options: the electrical potential of an ECG electrode; the electrical potential of a different temporary electrode or a potential formed by a combination of ECG electrode(s) and/or temporary electrode(s).

7. The method of claim 5 wherein at least one temporary electrode is located at any point on the right arm, shoulder or hand.

8. The method of claim 5 wherein at least one temporary electrode is located at any point on the left arm, shoulder or hand.

9. The method of claim 5 wherein the temporary electrode(s) are connected at a different time from when the first set of ECG signals is acquired, or equivalently, activated temporarily, and the subject-specific transformations retrospectively calculated.

10. The method of claim 5 wherein a temporary electrode, after initial use, is used to perform functions other than that of supplying electrocardiogram signal data.

11. The method of claim 5 wherein an input connection to a measurement means or device used to obtain a signal from an ECG electrode(s) has a secondary use to obtain a signal from a temporary electrode.

12. The method of claim 1 further comprising the step of switching an electrode between separate modes of operation wherein in a first mode, the electrode measures an ECG signal and in a second mode, the electrode forms a reference electrical connection between a subject and an ECG measurement means.

13. The method of claim 1 further comprising the step of applying a plurality of electrodes on a subject's body to enable the measurement of a set of ECG signals for that subject; detecting subject's body posture; and selecting or modifying the set of transformations on the basis of the subject's body posture.

14. The method of claim 13 wherein a posture of said body is detected by an accelerometer, tilt sensor or manual switch.

15. The method of claim 1 further comprising the steps of calculating a simulation matrix for at least one temporary signal from the first set of data or a subset thereof; applying a simulation matrix to the second set of ECG signals to generate a simulated temporary signal; applying a fixed derivation matrix to the second data set plus the simulated signal to define an unmeasured ECG lead; and adapting one or both of said matrices to compensate for subject specific variations in posture and movement.

16. The method of claim 1 further comprising measuring the first set of ECG signals, processing said signals to derive a standard 12 lead ECG and displaying said standard 12 lead ECG in real time.

17. The method of claim 16 wherein the first set of ECG signals is recorded and stored for later processing to derive a standard 12 lead ECG.

18. The method of claim 1 wherein right and left sites comprise sites RC and LC which are placed at the same level as the manubrium on the right and left mid-clavicular lines respectively.

19. A storage device carrying program instructions for causing a general purpose microprocessor or digital signal processor circuit to implement a method as claimed in claim 1.

* * * * *